(12) United States Patent
Johnson

(10) Patent No.: US 6,537,278 B1
(45) Date of Patent: Mar. 25, 2003

(54) APPARATUS FOR USE IN GRAFTING ARTICULAR CARTILAGE

(75) Inventor: Lanny L. Johnson, Okemos, MI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/593,037

(22) Filed: Jun. 13, 2000

Related U.S. Application Data

(62) Division of application No. 09/274,909, filed on Mar. 23, 1999, now Pat. No. 6,120,541.

(51) Int. Cl.[7] .............................................. A61B 17/32
(52) U.S. Cl. ........................ 606/79; 606/170; 606/167
(58) Field of Search ...................... 606/167, 79, 170; 81/3.41

(56) References Cited

U.S. PATENT DOCUMENTS

| | | | | |
|---|---|---|---|---|
| 544,463 A | * | 8/1895 | Devries ........................ 81/3.41 |
| 624,457 A | * | 5/1899 | Converse ..................... 81/3.41 |
| 854,812 A | * | 5/1907 | Dodge ......................... 81/3.41 |
| 893,055 A | * | 7/1908 | Conner ........................ 81/3.41 |
| 1,230,726 A | * | 6/1917 | Krause ........................ 81/3.41 |
| 1,350,383 A | * | 8/1920 | Paluhniuk ................... 81/3.41 |
| 2,484,043 A | * | 10/1949 | Malen ......................... 81/3.41 |
| 3,451,076 A | * | 6/1969 | Deaver ........................ 81/3.41 |
| 4,566,138 A | | 1/1986 | Lewis et al. |
| 5,192,298 A | * | 3/1993 | Smith et al. ................. 606/205 |
| 5,478,347 A | * | 12/1995 | Aranyi ........................ 606/170 |
| 5,571,184 A | | 11/1996 | DeSatnick |
| 5,649,945 A | * | 7/1997 | Ray et al. .................... 606/167 |
| 5,653,756 A | | 8/1997 | Clarke et al. |
| 5,725,580 A | | 3/1998 | Cloutier et al. |
| 5,989,277 A | * | 11/1999 | LeMaire, III et al. ...... 606/170 |
| 6,168,605 B1 | * | 1/2001 | Measamer et al. ........... 606/174 |
| 6,299,630 B1 | * | 10/2001 | Yamammoto ............... 606/205 |

* cited by examiner

*Primary Examiner*—David H. Willse
*Assistant Examiner*—Suzette J. Jackson

(57) ABSTRACT

A device for dovetailing a wall of a cavity formed in cartilage includes a handle from which a pair of flexible blades extend, the blades having outwardly bent distal ends provided with cutting edges. A spike, fixed to the handle in a position substantially coaxial with the handle's longitudinal axis, is disposed between the blades.

1 Claim, 1 Drawing Sheet

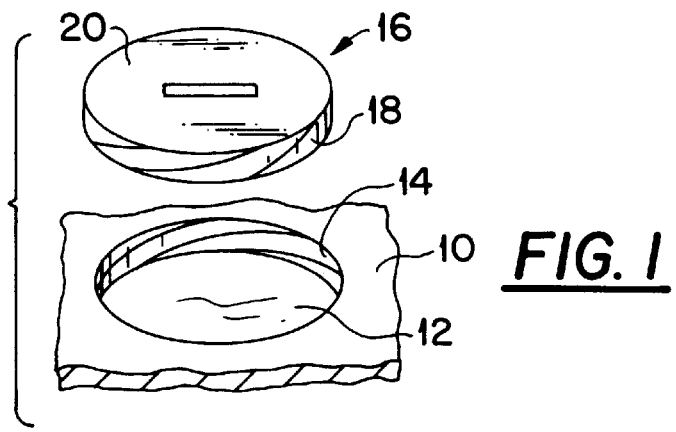
FIG. 1
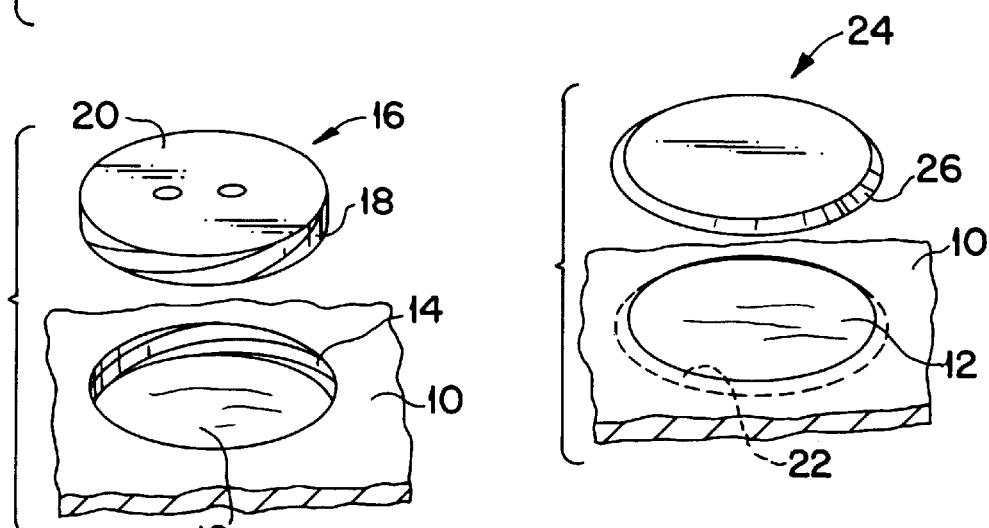
FIG. 3
FIG. 2
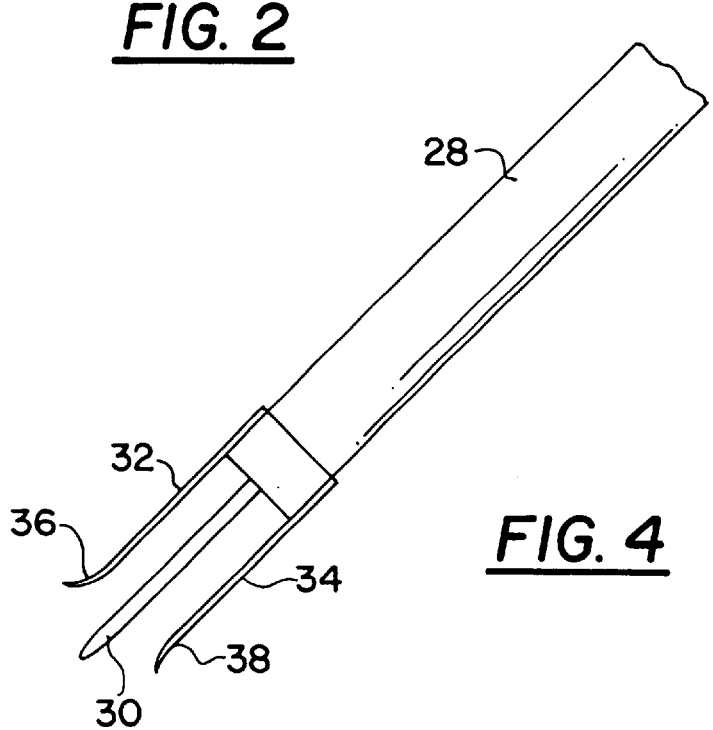
FIG. 4

APPARATUS FOR USE IN GRAFTING ARTICULAR CARTILAGE

This is a division of application Ser. No. 09/274,909, filed Mar. 23, 1999 now U.S. Pat. No. 6,120,541.

BACKGROUND OF THE INVENTION

1. Field of the Invention

The present invention relates to devices for securing articular cartilage grafts in place to facilitate successful healing of the graft.

2. Prior Art

Known methods of holding an articular cartilage graft in place involve suturing an overlying thin membrane periosteum, a synthetic, or a biological material to the area surrounding the defect being repaired by the graft. The sewn substance retains the graft in place while healing occurs. However, such a suturing technique is technically difficult, time consuming and imprecise.

SUMMARY OF INVENTION

The present invention overcomes the deficiencies of the suturing technique just described. More particularly, the defective area being repaired is first removed by a drilling operation leaving a cavity within which the graft is to be placed. The wall of the cavity is formed to receive and retain a cap. After the graft is properly positioned, the cap is secured within the cavity in overlying relationship with the graft so as to retain the graft in place during the healing process.

BRIEF DESCRIPTION OF THE DRAWINGS

The invention now will be described in greater detail by reference to the accompanying drawings, wherein:

FIG. 1 illustrates a first embodiment of a cap for retaining an articular cartilage graft in place;

FIG. 2 is an alternative embodiment of the cap shown in FIG. 1;

FIG. 3 is a still further embodiment of an articular cartilage graft retaining device; and FIG. 4 illustrates an instrument for preparing a cavity to receive the graft retaining device shown in FIG. 3.

DETAILED DESCRIPTION OF PREFERRED EMBODIMENTS OF THE INVENTION

FIGS. 1 and 2 depict an area 10 of articular cartilage which is to be repaired. A defective area in the cartilage is removed by a conventional drill to form a cavity 12. The wall 14 of the cavity is threaded by a tap. A cap 16 is provided to be received with cavity 12. The cap is a thin, disk-shaped member having a peripheral edge 18 threaded complementary to the thread formed in wall 14 of the cavity 12. The upper surface 20 of cap 16 is slotted (FIG. 1) or is provided with a pair of spaced holes (FIG. 2) to receive a tool which is used to screw the cap 16 within the cavity 12.

In use, after cavity 12 is formed and its wall is tapped, an articular cartilage graft is positioned within the cavity. The cap 16 is then screwed into cavity 12 to overlie the graft and retain it in position. With the graft held securely in place under compression, the side of the graft opposite cap 16 will heal to the adjacent cartilage.

An alternative type of cap is illustrated in FIG. 3. In this case, no thread is formed in cavity 12. Instead, the wall 22 of the cavity is dovetailed. A flexible disk-shaped cap 24 is dimensioned to be received within cavity 12. More particularly, the peripheral edge 26 of cap 24 is formed to be complementary with the dovetailed wall of the cavity. In use, and with the articular cartilage graft in place within cavity 12, the flexible cap 24 is folded and is inserted within the cavity. When the cap is released, its resiliency causes it to return to its disk-like shape whereby its peripheral edge 26 lies within the dovetailed wall 22 of the cavity. Thus, the graft is retained in position during the healing process.

An instrument suitable for forming a dovetail in the wall 22 of cavity 12 is shown in FIG. 4. More particularly, a handle 28 is provided at its distal end with a projecting fixed spike 30 located coaxially with the longitudinal axis of the handle. At least two flexible blades 32 and 34 extend from the distal end of handle 28, the blades being secured to the periphery of the handle. The blades are provided with outwardly bent cutting edges 36 and 38 at their extremities.

In operation, the blades are flexed inwardly from the position shown in FIG. 4 towards spike 30. The spike is used to center the knife within a cavity (such as cavity 12 in FIG. 3). The blades are then released whereby their resiliency causes them to move against the wall of the cavity. As handle 28 is rotated, cutting edges 36 and 38 dovetail the wall of the cavity.

The instrument just described has spike 30 and/or blades 32 and 34 permanently attached to handle 28. Alternatively, at least blades 32 and 34 can be removably secured to the handle by conventional means so as to be disposable.

What is claimed is:

1. A device for dovetailing a wall of a cavity formed in cartilage, said device comprising:

a handle;

at least two flexible blades joined to, and projecting beyond, a distal end of the handle, said blades being offset from an axis passing through the handle and having distal ends, each of which is bent outwardly in opposite directions relative to said axis and is provided with a cutting edge on an outward side of its distal end; and a spike positioned between the blades and projecting from said distal end of the handle substantially along the axis that passes through the handle;

wherein the device forms a dovetail cut in cartilage when said device is rotated about the axis that passes through the handle.

* * * * *